US009492338B2

(12) United States Patent
Miyachika et al.

(10) Patent No.: US 9,492,338 B2
(45) Date of Patent: *Nov. 15, 2016

(54) PRESSURE-SENSITIVE ADHESIVE TAPE PACKAGE

(75) Inventors: Takafumi Miyachika, Tosu (JP); Hiroyuki Taketomi, Tosu (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 81 days.

This patent is subject to a terminal disclaimer.

(21) Appl. No.: 14/112,775

(22) PCT Filed: Mar. 21, 2012

(86) PCT No.: PCT/JP2012/057205
§ 371 (c)(1),
(2), (4) Date: Apr. 30, 2014

(87) PCT Pub. No.: WO2012/144287
PCT Pub. Date: Oct. 26, 2012

(65) Prior Publication Data
US 2014/0231292 A1 Aug. 21, 2014

(30) Foreign Application Priority Data

Apr. 22, 2011 (JP) .............................. P2011-096574

(51) Int. Cl.
*A61F 15/00* (2006.01)
*A61F 13/00* (2006.01)
(52) U.S. Cl.
CPC ......... *A61F 15/001* (2013.01); *A61F 13/0008* (2013.01)
(58) Field of Classification Search
CPC ............................ A61F 15/001; A61F 13/0008
(Continued)

(56) References Cited

U.S. PATENT DOCUMENTS 4,265,234 A   5/1981   Schaar
7,523,821 B2   4/2009   Assie et al.
(Continued)

FOREIGN PATENT DOCUMENTS

EA        010078 B1    6/2008
EP        0372722 A2   6/1990
(Continued)

OTHER PUBLICATIONS

Japanese Patent Application No. P2013-510921, Notice of Allowance issued Jun. 17, 2014, three (3) pages.
(Continued)

*Primary Examiner* — Anthony Stashick
*Assistant Examiner* — Raven Collins
(74) *Attorney, Agent, or Firm* — Nath, Goldberg & Meyer; Joshua B. Goldberg; Tanya E. Harkins

(57) ABSTRACT

A novel pressure-sensitive adhesive tape package easy to open and easy in application of an adhesive tape is disclosed. The pressure-sensitive adhesive tape package 10 according to the present invention includes an adhesive tape 14 that accommodates a support 18 and an adhesive agent layer 12 provided on one surface of the support 18, and a release sheet 16 releasably attached to the adhesive agent layer 12. Moreover, the release sheet 16 is folded with the adhesive tape 14, and the adhesive tape 14 is sealed inside of the folded release sheet 16. A plurality of temporary attach portions 50 to 54 spaced from each other is provided in a half of the adhesive agent layer 12 in the adhesive tape 14 to securely expose the half when the release sheet 16 is opened.

11 Claims, 7 Drawing Sheets

(58) Field of Classification Search
USPC .......... 206/440, 441, 430, 438; 156/249
See application file for complete search history.

(56) References Cited

U.S. PATENT DOCUMENTS

2006/0163101 A1 7/2006 Assie et al.
2011/0253304 A1* 10/2011 Ohta et al. ............ 156/249

FOREIGN PATENT DOCUMENTS

| EP | 0683216 A1 | 11/1995 |
|---|---|---|
| JP | S50-133797 | 11/1975 |
| JP | 2001104367 A | 4/2001 |
| JP | 2003325575 A | 11/2003 |
| JP | 3689807 B2 | 8/2005 |
| JP | 2006516414 A | 7/2006 |
| JP | 2007-075601 | 3/2007 |
| JP | 2007-075602 | 3/2007 |
| JP | 5276608 B2 | 8/2013 |
| JP | 5371806 B2 | 12/2013 |
| RU | 98115136 A | 6/2000 |
| RU | 2008140319 A | 4/2010 |
| WO | 97/25012 A1 | 7/1997 |
| WO | 01/35884 A1 | 5/2001 |
| WO | 2004056345 A1 | 7/2004 |
| WO | 2005/051650 A2 | 6/2005 |
| WO | 2010071104 A1 | 6/2010 |
| WO | 2010073993 A1 | 7/2010 |

OTHER PUBLICATIONS

Search Report issued in International Application No. PCT/JP2012/057205 mailed Jun. 12, 2012, 2 pages.
Singapore Patent Application No. 2013078167, Search Report dated Dec. 12, 2014, fourteen (14) pages.
European Patent Application No. 12773765.8, Extended European Search Report dated Aug. 20, 2014, four (4) pages.
Translation of the International Preliminary Report on Patentability and Written Opinion issued in International Application No. PCT/JP2012/057205 dated Nov. 19, 2013, 5 pages.
Philippines Patent Application No. 1-2013-502176, Office Action dated Mar. 12, 2015, four (4) pages.
Chinese Patent Application No. 201280019604.X, Office Action dated Jun. 30, 2014, five (5) pages.
Russian Patent Application No. 2013152019, Notice of Allowance dated Jan. 21, 2016, seven (7) pages.

* cited by examiner (a)

(b)

(c)

(a)

(b)

(a)

(b)

(a)

(b)

(c)

US 9,492,338 B2

PRESSURE-SENSITIVE ADHESIVE TAPE PACKAGE

TECHNICAL FIELD

This is a National Phase Application filed under 35 U.S.C. §371 as a national stage of International Application No. PCT/JP2012/057205 filed Mar. 21, 2012, claiming the benefit from Japanese Patent Application No. 2011-096574, filed Apr. 22, 2011, the entire content of each of which is hereby incorporated by reference in its entirety.

The present invention relates to a package that packs an adhesive tape having an adhesive agent layer on a support.

BACKGROUND ART

Adhesive tapes in a variety of forms have conventionally been known and used for labels, medical care, cosmetics, decoration, masking, electronic industries, and other various applications. The adhesive tape used for medical care is in a form of a patch preparation such as a poultice, a plaster, an adhesive bandage, and a surgical tape, and usually applied onto a skin, a mucous membrane, or the like.

Such an adhesive tape usually comprises an adhesive tape having a support and an adhesive agent layer provided on one surface of the support, and a release sheet releasably attached to the adhesive agent layer. The adhesive tape, after production, may be cut into an appropriate size and distributed and sold in the state of being individually contained in a package for hygienic and physical protection. In this case, at the time of use thereof, the adhesive agent layer is applied onto a portion for application after tearing the package to remove the adhesive tape therefrom, and release the release sheet to expose the adhesive agent layer.

A problem that often occurs at the time of use is difficulties in releasing the release sheet. Because the release sheet is usually thin and soft, it is difficult to handle, and it may take some time to release the release sheet. In order to improve this point, for example, as disclosed in the following Patent Literatures 1 to 4, a variety of release sheets and adhesive tapes have been developed in which easiness in releasing the release sheet and easiness in applying the adhesive tape are pursued.

Each of these release sheets or adhesive tapes has a structure such that convenience is pursued from the viewpoint of easiness in applying the adhesive tape. It is certainly convenient, but there is no difference in that the adhesive tape maintains the form including the release sheet and the package, and the release sheet and the package are turned into a waste after use.

Then, a pressure-sensitive adhesive tape package described in Patent Literature 5 or Patent Literature 6 has been proposed in the related art. The package is a package in which an adhesive tape is folded into two such that an adhesive agent layer faces outwardly, the two-folded adhesive tape is covered with a release sheet so as to sandwich the adhesive tape inside of the release sheet, and the periphery of the release sheet is sealed. In this configuration, the release sheet functions as a package, and thus the package needed in the related art can be eliminated.

Moreover, to expose only a half of the adhesive agent layer when the front portion of the release sheet is pulled off from the rear portion thereof to open the package, means for temporarily attaching the half located on the front side of the two-folded adhesive tape to the rear portion of the release sheet is provided. Thereby, application to a portion for application is easy because when the package is opened, the adhesive tape folded in two is held by the front portion of the release sheet and the half on the front side of the adhesive agent layer is exposed.

CITATION LIST

Patent Literature

Patent Literature 1: Japanese Patent Application Laid-Open No. 2007-75602
Patent Literature 2: Japanese Patent Application Laid-Open No. 2007-75601
Patent Literature 3: Japanese Patent No. 3689807
Patent Literature 4: Japanese Utility Model Laid-Open No. 50-133797
Patent Literature 5: WO2010/071104
Patent Literature 6: WO2010/073993

SUMMARY OF INVENTION

Technical Problem

The above package described in Patent Literature 5 or Patent Literature 6 is excellent, but further improvement in usage, production, and the like is demanded.

Solution to Problem

To solve the problems above, the present invention is a rectangular pressure-sensitive adhesive tape package accommodating an adhesive tape having a support and an adhesive agent layer provided on one surface of the support, the pressure-sensitive adhesive tape package comprising a first portion and second portion formed of a release sheet releasably attached to the adhesive agent layer, the first portion and the second portion being layered, a periphery of the layered first portion and second portion being sealed, wherein a first sealed portion along a first edge in the pressure-sensitive adhesive tape package, a second sealed portion extending along a second edge adjacent to the first edge and crossing the first sealed portion, and a third sealed portion extending along a third edge adjacent to the first edge and crossing the first sealed portion are spaced from the corresponding edges; the adhesive tape is accommodated in the pressure-sensitive adhesive tape package such that the adhesive agent layer faces outwardly in a state where the adhesive tape is folded into a first portion and a second portion; the first portion of the adhesive tape is larger than the second portion of the adhesive tape, and has an extending portion extending from the second portion; and the extending portion is disposed adjacent to the first sealed portion, and temporarily attached to a portion of the release sheet that is to be the second portion side of the adhesive tape.

In such a configuration, the first to third sealed portions are spaced from the corresponding edges. For this reason, when opening the package is started from a portion between the first sealed portion and the first edge, an opening force easily concentrates on the corner of the first sealed portion and second sealed portion or third sealed portion crossing, and the sealed portion can be broken with a small force to open the package. In the package above described in Patent Literature 5 or Patent Literature 6, no space is provided between the second and third sealed portions and the corresponding edges. In this case, the force in opening the package acts to the linear portion of the first sealed portion to be dispersed, and a considerable amount of the force is needed to open the package. In the present invention, such a problem will not arise.

To further facilitate opening the package, it is preferable that the interval between the first edge and the first sealed portion is used as a holding portion.

Moreover, when the package is opened, the first portion of the adhesive tape is held by the release sheet on the second portion side by existence of the temporary attach portions in the adhesive tape to expose only a half of the adhesive agent layer. However, in the configuration of the present invention, as described above, the package is opened from the crossing corner of the first sealed portion and the second sealed portion. For this reason, it is thought that the first portion of the adhesive tape is not held only by the temporary attach portions parallel to the first sealed portion unlike the package described in Patent Literature 5 or Patent Literature 6. Then, in the present invention, the temporary attach portions are provided in not only along the first sealed portion but also along the second sealed portion and the third sealed portion.

Furthermore, in the present invention, the temporary attachment is performed in dots or discontinuously. Namely, small temporary attach portions are provided in a plurality of places such that adjacent temporary attach portions are spaced from each other. Considering application to the portion for application, the adhesive force of the support in the adhesive tape to the release sheet via the temporary attach portions needs to be larger than the adhesive force of the adhesive agent layer to the release sheet. In the case where the temporary attach portion is a continuous band-like portion with a large area, the adhesive force of the adhesive tape to the support tends to be larger. Moreover, the adhesive force is difficult to adjust. Contrary to this, in the case where a plurality of small temporary attach portions is discontinuously disposed as in the present invention, the adhesive force can be reduced. Moreover, the adhesive force can be easily controlled by adjusting the number and size of temporary attach portions.

In the case where a layer of the release sheet to be located inside of the pressure-sensitive adhesive tape package is formed of a thermoplastic material, the temporary attach portions can be provided by thermal bonding of the layer formed of the thermoplastic material to the support of the adhesive tape. In the case where the first to third sealed portions are heat-sealed portions, this can perform heat seal and thermal bonding continuously or simultaneously to attain an effect of significantly improving production efficiency.

It is preferable that means for reducing an adhesive force to suppress the adhesive force between the adhesive agent layer in the first portion of the adhesive tape and the release sheet is provided in at least a part of the release sheet. When the package is opened, the adhesive agent layer is easily separated from the release sheet to expose the adhesive agent layer, and therefore application to the portion for application is easy.

The material and configuration of the release sheet is not particularly limited as long as the adhesive agent layer of the adhesive tape can be protected until the adhesive tape is used, but the configuration in which a cellophane film, a plastic film, and an aluminum foil from the outer layer and further a plastic film in the inner layer are laminated is preferable; further, it is preferable that the means for suppressing an adhesive force is a silicone-treated surface provided on at least a part of a portion of the release sheet that is applied to the adhesive agent layer of the first portion of the adhesive tape. Among a variety of means for suppressing an adhesive force, the silicone treatment is advantageous in that the treatment is performed relatively easily and at low cost. As another means for suppressing an adhesive force, embossing and/or sanding may be performed on the portion.

The package according to the present invention facilitates application to the portion for application, and therefore it is effective that the adhesive tape is used for a skin or a mucous membrane.

Moreover, as the package according to the present invention, the so-called three-sealed package type, namely, the case where the first portion of the release sheet and the second portion thereof fold one release sheet and the three sides are sealed, and the so-called four-sealed package type, namely, the case where the first portion of the release sheet and the second portion thereof are formed of individual release sheets, respectively, and the four sides are sealed are typical.

Advantageous Effects of Invention

As described above, application to the portion for application is easy according to the present invention because to open the package is easy, and the half of the adhesive agent layer in the adhesive tape can be surely exposed. Additionally, after the half of the release sheet is released off, the adhesive tape is supported or reinforced on the remaining portion of the release sheet; for this reason, this prevents the adhesive agents from adhering to each other to cause a state where the adhesive tape cannot be used, and application is easy. Moreover, in the case where the adhesive tape is a patch preparation that can be applied to a human body, such as a plaster preparation, a poultice, a plaster, an adhesive bandage, a surgical tape, an adhesive chemical heating pack or the like, the adhesive tape can be easily applied by a single hand without getting a hand dirty even if the portion for application is a back or the like in which application is difficult by oneself.

Moreover, according to the pressure-sensitive adhesive tape package according to the present invention, the adhesive force of the temporary attach portion can be easily adjusted, and therefore production efficiency is improved and stable function can be ensured.

DESCRIPTION OF EMBODIMENTS

Figure 1:
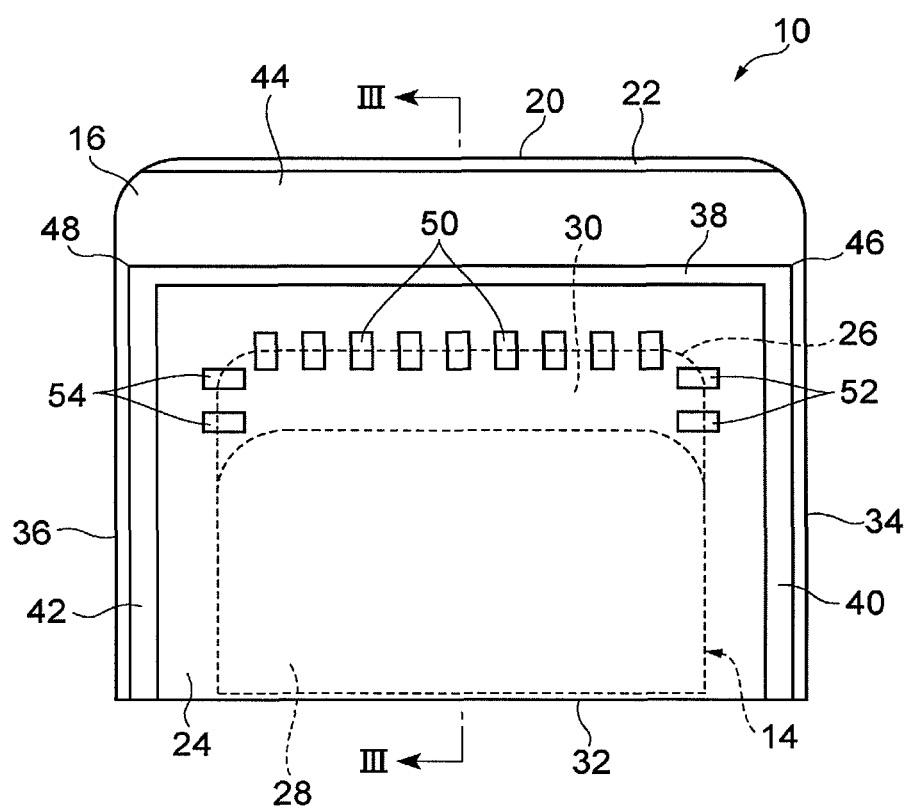
FIG. 1 is a front view of a pressure-sensitive adhesive tape package according to one embodiment of the present invention.

Hereinafter, with reference to the drawings, suitable embodiments according to the present invention will be described. Through all the drawings, same reference numerals will be given to same or equivalent portions, and the duplicate description thereof will be omitted.

FIG. 1 is a front view showing a pressure-sensitive adhesive tape package 10 according to a suitable embodiment of the present invention, and FIGS. 2(a) to 2(c) are perspective views showing production steps of the pressure-sensitive adhesive tape package 10 in FIG. 1. FIG. 3 is a schematic sectional view taken along the line III-III in FIG. 1.

The shown pressure-sensitive adhesive tape package 10 includes an adhesive tape 14 having an adhesive agent layer 12 on one surface thereof, and a release sheet 16 for sealing the adhesive tape 14 folded in two. The adhesive tape 14 and the release sheet 16 both are rectangular. As understood from FIG. 1 and FIG. 2(c), the pressure-sensitive adhesive tape package 10 is the so-called three-sealed package type in which one release sheet 16 is folded, and three sides except the bend side are sealed.

The pressure-sensitive adhesive tape package 10 is used for labels, medical care, cosmetics, decoration, masking, electronic industries, and other various applications. Particularly, the pressure-sensitive adhesive tape package used for medical care, cosmetics, and the like can be used as a package of a patch preparation such as a plaster, a poultice, an adhesive bandage, a surgical tape, a cosmetic face pack preparation, and an adhesive heating pack that is usually applied to a skin, a mucous membrane, and the like.

As shown in FIG. 3, the adhesive tape 14 includes a support 18, and the adhesive agent layer 12 laminated on the one surface thereof, and the release sheet 16 is releasably attached to this. The component material of the support 18 is not particularly limited as long as it can support the adhesive agent layer 12, and usually, woven fabrics, non-woven fabrics, films made of a plastic or the like, metallic foils, and the like are used. Further, the support may be a single layer structure or a laminate structure; it may be a structure in which a plurality of woven fabrics or non-woven fabrics made of different materials is laminated, or a structure in which a plastic film, a metallic foil, or the like and a woven fabric or a non-woven fabric are laminated, for example.

Moreover, the woven fabric or non-woven fabric used for the present invention is not particularly limited, and may be those obtained by processing a fibrous material into a fabric and applicable for the support of the adhesive tape; examples thereof include a knitted fabric processed into a fabric by collecting stitches by warp knit, weft knit, and the like.

Preferable examples of the woven fabric or non-woven fabric include woven fabrics or non-woven fabrics made of at least one kind of resin fibers selected from the group consisting of polyester resins, polyethylene resins, and polypropylene resins; among them, the woven fabrics made of polyethylene terephthalate that is polyester with less interaction with the component contained in the adhesive agent layer are preferable.

Examples of the plastic film include those formed using polyesters such as polyethylene terephthalate, polyamides such as nylon, polyolefins such as polyethylene and polypropylene, polyvinyl chloride, plasticized polyvinyl chloride, plasticized vinyl acetate-vinyl chloride copolymers, polyvinylidene chloride, ethylene-vinyl acetate copolymers, cellulose acetate, ethyl cellulose, ethylene-ethyl acrylate copolymers, polytetrafluoroethylene, polyurethanes, and ionomer resins. Moreover, in the case where the adhesive tape of the present invention is used as the patch preparation for medical care or cosmetics, it is preferable that a material having sufficient stretchability or non-stretchability as a patch preparation is used for the support, and a polyethylene terephthalate hosiery woven fabric (knitted fabric) is particularly preferable.

It is preferable that in the knitted fabric as the support 18, the basis weight (mass per units) is 50 to 500 g/m$^2$. Moreover, in the case where the support 18 is measured according to the method of JIS L1096, it is preferable that the modulus at 30% strain in the longitudinal length (long axis direction) is 2 to 12 N/5 cm, and the modulus at 30% strain in the traverse direction (short axis direction) is also 2 to 12 N/5 cm. The longitudinal length here refers to a flow direction at a step of producing a knitted fabric, and the traverse direction refers to a direction perpendicular to the longitudinal length, namely the width direction. In the case where the modulus at 30% strain is smaller than 2 N/5 cm in the longitudinal length or traverse direction, application to the portion for application while unwrinkling tends to be difficult; moreover, in the case where the modulus at 30% strain is larger than 12 N/5 cm in the longitudinal length or traverse direction, conversely, the adhesive tape tends to be excessively stretched during application to cause wrinkles. The modulus at 30% strain is a value at room temperature (25° C.).

By use of the support 18 above, temporary attaching by the temporary attaching means described later is facilitated, and the shape and structure of the support 18 after the support is removed from the temporary attaching are hardly changed. Namely, fuzzing or the like is not produced, for example. Moreover, bending the pressure-sensitive adhesive tape package 10 into two is easy, and the bent pressure-sensitive adhesive tape package is not bulky. Further, the so-called "kink" is hardly produced in the portion that is bent into two during application, and the adhesive tape is applied neatly.

The adhesive component that is the component material of the adhesive agent layer 12 is not particularly limited as long as it has adhesiveness and can be applied to the portion for application; acrylic adhesive components, rubber based adhesive components, silicone based adhesive components, and the like are preferably used as an adhesive base; among them, the rubber based adhesive components are particularly preferably used from the viewpoint of adhesiveness.

As a specific example of the rubber based adhesive component, natural rubbers and synthetic rubbers both can be used, and examples of the synthetic rubbers include styrene block copolymers and polyisobutylene. Further, examples of the styrene block copolymers include styrene-butylene-styrene block copolymers (SBS), styrene-isoprene-styrene block copolymers (SIS), styrene-ethylene/butylene-styrene block copolymers (SEBS), and styrene-ethylene/propylene-styrene block copolymers (SEPS). Specific examples of the styrene block copolymers include linear triblock copolymers such as Kraton D-1112, D-1111, and D-1107 (trade name, made by Kraton Performance Polymers Inc), JSR5000 or JSR5002 (trade name, made by JSR Corporation), Quintac 3530, 3421 or 3570C (trade name, made by Zeon Corporation), and Kraton D-KX401CS or D-1107CU (trade name, made by Kraton Performance Polymers Inc), and branched block copolymers such as Kraton D-1124 (trade name, made by Kraton Performance Polymers, Inc.) and Solprene 418 (trade name, made by Phillips Petroleum Company).

As polyisobutylene, for example, high or low molecular weight are used, and examples thereof include Oppanol B10, B12, B12SF, B15, B15SF, B30SF, B50, B50SF, B80, B100, B120, B150, and B200 (trade name, made by BASF SE), and Vistanex LM-MS, LM-MH, LM-H, MM L-80, MM L-100, MM L-120, and MM L-140 (trade name, made by Exxon Chemical Company).

Moreover, as the acrylic polymer, a polymer or copolymer containing at least one (meth)acrylate ester such as 2-ethylhexyl acrylate, methyl acrylate, butyl acrylate, hydroxyethyl acrylate, 2-ethylhexyl-methacrylate as a monomer unit is used, and acrylic acid/acrylic acid octyl ester copolymers, 2-ethylhexyl acrylate/N-vinyl-2-pyrrolidone/1,6-hexaneglycol dimethacrylate copolymers, 2-ethylhexyl acrylate/vinyl acetate copolymers, 2-ethylhexyl acrylate/vinyl acetate/acrylic acid copolymers, 2-ethylhexyl acrylate/2-ethylhexyl-methacrylate/dodecyl methacrylate copolymers, a methyl acrylate/2-ethylhexyl acrylate co polymerized resin emulsion, an adhesive agent of an acrylic polymer or the like contained in an acrylic resin alkanolamine solution, DUROTAK acrylic adhesive agent series (made by National Starch and Chemical Company), GELVA acrylic adhesive agent series (made by Monsanto Company), SK-Dyne Matriderm (Soken Chemical & Engineering Co., Ltd.), EUDRAGIT series (Higuchi Inc.), and the like can be used, for example.

One of the adhesive bases such as the rubber adhesive base, the acrylic adhesive base, and the silicone adhesive base above can be used, or two or more thereof can be mixed and used.

Further, in the case where the adhesive tape of the present invention is used as a poultice or a plaster for medical care or a cosmetic face pack agent, a water-soluble polymer can also be used as the adhesive agent layer; as such a water-soluble polymer, gelatin, agar, alginic acid, mannan, carboxymethyl cellulose or salts thereof, hydroxypropyl cellulose or salts thereof, polyvinyl alcohol, polyacrylic acid or salts thereof, and the like, or those obtained by crosslinking at least one of these by an organic or inorganic crosslinking agent are preferably used.

Other than the adhesive bases above, a tackifier, a softening agent, a solvent, water, a thickener, a wetting agent, a filler, a crosslinking agent, a polymerizing agent, a solubilizing agent, an absorption promoter, a stabilizer, an antioxidant, an emulsifier, a surface active agent, a pH adjuster, drugs, an ultraviolet absorbing agent, and the like are properly added to the adhesive agent layer.

The drugs in the case where the adhesive tape of the present invention is used as the patch preparation for medical care and cosmetics are not particularly limited as long as they are percutaneously absorbed into the body to demonstrate a pharmacological effect, and examples thereof include an antiinflammatory agent, an analgesic agent, an antihistamine, a local anesthetic agent, a blood circulation promoter, an anesthetic agent, a tranquilizer, an antihypertensive agent, an antibacterial agent, and a vasodilator.

The release sheet 16 of the present invention can be used if it is those usually used as the package of the adhesive tape. Moreover, the release sheet 16 may be a single layer or a laminated layer, and the material that forms the release sheet is not particularly limited if the advantageous effects of the present invention are obtained. For example, the material can be properly selected from paper, a non-woven fabric, aluminum, cellophane, nylon, high density or low density polyethylene, polyethylene terephthalate, polypropylene, polyvinyl chloride, polyamide, polyvinylidene chloride, polyvinyl alcohol, polyvinyl acetate copolymers, polycarbonate, polystyrene, ethylene vinyl alcohol copolymers, and the like.

Further, the release sheet may be those in which a printing ink or an adhesive is applied, or those on which a thin film is provided by a method such as deposition or sputtering. As the thin film, thin films with high gas barrier properties and transparency made of silicon oxide, magnesium oxide, and aluminum oxide other than metals such as aluminum are suitable. Among these, the film containing aluminum is preferable, those in which further polyethylene, aluminum, polyethylene are sequentially laminated are more preferable, and those in which cellophane is also further laminated on the outermost layer are preferable for use.

Because these release sheets are bent when the adhesive tape is sealed, those having flexibility are preferable. Accordingly, the thickness of the release sheet is not particularly limited as long as it can be bent, and it is preferable that the thickness is in the range of 10 to 500 µm, and it is more preferable that the thickness is in the range of 15 to 300 µm.

Here, returning to the production steps, first, as shown in FIG. 2(a), the adhesive tape 14 is releasably attached onto the release sheet 16 with the adhesive agent layer 12 facing downwardly. At this time, the adhesive tape 14 is attached to the release sheet 16 in a state where the center line parallel to the short direction of the adhesive tape 14 may be displaced from the center line parallel to the short direction of the release sheet 16.

Figure 2:
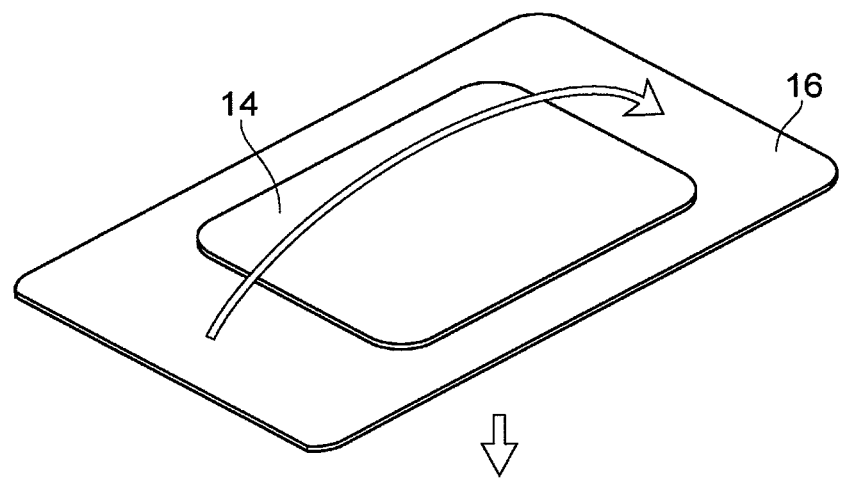
FIGS. 2(a) to 2(c) are perspective views showing production steps of the pressure-sensitive adhesive tape package in FIG. 1.
Figure 2:
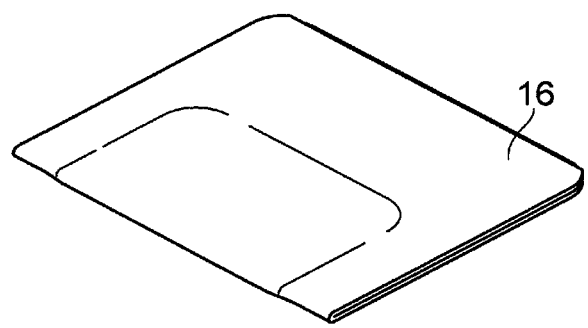
Figure 2:
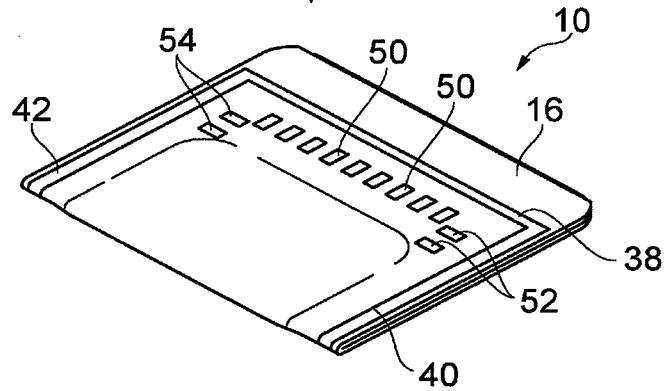
Figure 3:
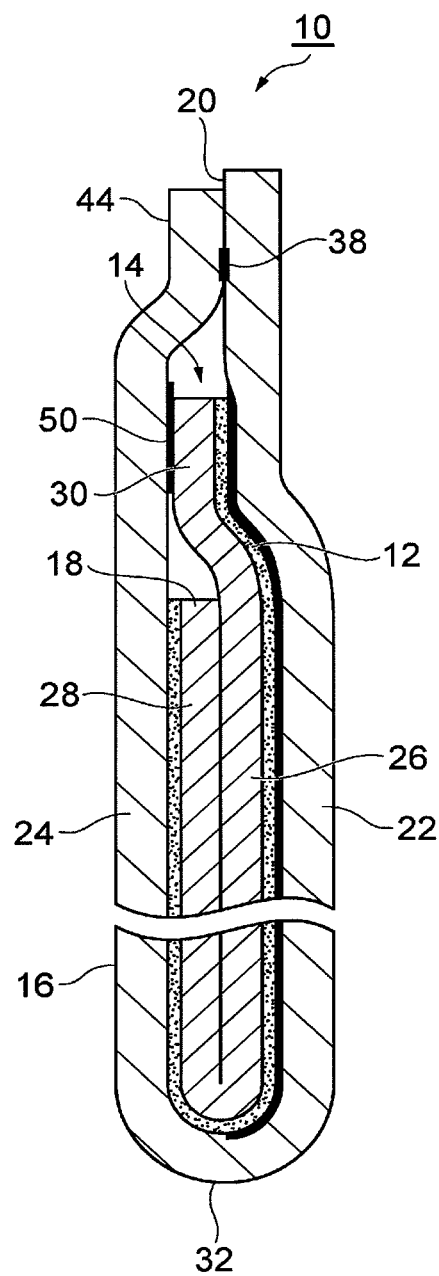
FIG. 3 is a schematic sectional view taken along the line III-III in FIG. 1.

Next, the release sheet 16 is folded with the adhesive tape 14 into a state shown in FIG. 2(b). The bending position of the release sheet 16 may be on the center line in the short direction of the release sheet 16, but it is preferable that the bending position is a position slightly displaced from the center line. By slightly displacing the bending position from the center line and folding the release sheet 16, the edge of the release sheet 16 opposite to the bending edge (first edge) 20 is displaced as schematically shown in FIG. 3 to provide an effect of easily holding the first edge. For this displacement, various modifications can be thought in consideration of handling properties of the pressure-sensitive adhesive tape package 10. For example, a form in which the edge 20 of the first portion 22 in the release sheet 16 is projected from the edge 20 of the second portion 24 therein is used in the configuration shown in FIG. 1 and FIG. 2, but conversely the edge 20 of the second portion 24 may be projected from the first portion 22. Alternatively, a form in which a displacement portion is formed only in a corner of the package 10, or the first portion 22 is projected from the second portion 24 in the right half and the second portion 24 is projected from the first portion 22 in the left half may be used.

Here, assume that a half of the folded release sheet 16 is referred to as the first portion 22, the other half thereof is referred to as the second portion 24, a half of the adhesive tape 14 folded with the release sheet 16 is referred to as a first portion 26, and the other half thereof is referred to as a second portion 28. When the release sheet 16 is folded, the first portion 22 and the second portion 24 of the release sheet 16 have substantially the same shape and size except the displacement of the edge 20, while the adhesive tape 14 is in the state where the first portion 26 is larger than the second portion 28 and the first portion 26 has an extending portion 30 extending from the second portion 28 (FIG. 3).

In this state, of the portion of the release sheet 16 in which the first portion 22 is layered on the second portion 24, the three sides surrounding the adhesive tape 14 are sealed (FIG. 2(*c*)). More specifically, linear sealed portions 38, 40, and 42 are provided along the edge 20 opposite to the bending edge 32 of the release sheet 16, and edges 34 and 36 provided on both sides of the bending edge 32 (second edge 34 and third edge 36), respectively. The linear sealed portions 38, 40, and 42 are spaced from the corresponding edges 20, 34, and 36. Particularly, the distance from edge 20 to the sealed portion 38 (first sealed portion) along the edge 20 is longer than the distance from the edge 20 to the sealed portion 40 (second sealed portion 40) along the edge 34 and the distance from the edge 20 to the sealed portion 42 (third sealed portion 42) along the edge 36. Thereby, the outer portion from the sealed portion 38 functions as a holding portion 44. The holding portion is easy to hold with fingers, and opening the package is easy. As described above, the edges 20 of the first portion 22 and the second portion 24 in the release sheet 16 are slightly displaced to facilitate separation of the layered portion of the release sheet 16 that forms the holding portion 44, and the package is easier to open.

The sealed portions 38, 40, and 42 are linear, and approximately right-angled corners 46 and 48 are formed in their cross portions. The corners 46 and 48 are also spaced from the edges 20, 34, and 36. Although described in detail below, the corners 46 and 48 are spaced from the edges 20, 34, and 36 to attain an effect of concentrating a force on this portion and much facilitating opening the package.

As a method for forming the sealed portions 38, 40, and 42, a heat sealing method is suitable. Other than the heat sealing method, methods using an adhesive and the like can be thought. Moreover, use of the so-called easy peel techniques is also effective. The easy peel means easy releasabilty as described in the Patent Map for Technical Fields, General 21 "Adhesion," p. 335, available from the Japan Patent Office website (www.jpo.go.jp/shiryou/s_sonota/map/ippan21/4/4-3-1.htm), and refers to containers and packages sealed by heat sealing to provide easy releasing upon opening. Specifically, examples of easy peel include various types such as a cohesive failure type in which the adhesive layer between the first portion 22 and second portion 24 of the release sheet 16 itself is broken to be released off, an interlayer releasing type in which adhesive strength between the adhesive layer and the first portion 22 or second portion 24 is small, and the first portion 22 or the second portion 24 is released off from the adhesive layer at the time of opening, and an interlayer releasing type using an easy-releasable resin such as EVA, but are not particularly limited thereto; in the case where a sheet material in which a polyethylene layer is disposed on the surface is used as the release sheet 16, those with a two-layered structure composed of a resin layer containing a high density polyethylene as a principal component and an easy peel resin layer prepared by adding a resin causing the cohesive failure to a low density polyethylene, for example, may be used as an easy peel adhesive layer.

By forming the sealed portions in the three sides of the portion in which the release sheet 16 is folded to layer the first portion 22 and the second portion 24, the inside of the release sheet 16 is shielded from the outer world. For this reason, advantages are attained such that the adhesive tape 14 is more hygienically and physically protected, and the component contained in the adhesive agent layer 12 in the adhesive tape 14 does not leak to the outer world or volatize. Moreover, because the release sheet 16 also functions as the package, the separate package existing in the related art can be eliminated.

In order to avoid a pointed corner of the finished pressure-sensitive adhesive tape package 10, it is effective that the release sheet has a shape such that part of the corners and preferably all four corners of the finished pressure-sensitive adhesive tape package 10 may be in a round shape. The adhesive tape package 10 in FIG. 1 and FIG. 2(*c*) shows the state where two corners are round.

In such a pressure-sensitive adhesive tape package 10, when the first portion 22 of the release sheet 16 is pulled off from the second portion 24 thereof to open the package, the adhesive agent layer 12 in the two-folded adhesive tape 14 faces outwardly. Accordingly, the adhesive agent layer 12 in the first portion 26 in the adhesive tape 14 is exposed to the outside.

However, if the first portion 26 of the adhesive tape 14 moves together with the first portion 22 of the release sheet 16 and the adhesive agent layer 12 in the second portion 28 of the adhesive tape 14 is exposed, whether the adhesive agent layer 12 is exposed on the front side or rear side cannot be known, and this is inconvenient. Namely, it is important to primarily hold the first portion 26 of the adhesive tape 14 by the second portion 24 of the release sheet 16 when the package is opened, and expose the adhesive agent layer 12 in the first portion 26 of the adhesive tape 14. Then, the extending portion 30 formed on the first portion 26 of the adhesive tape 14 is temporarily attached to the second portion 24 of the release sheet 16 at places indicated by symbols 50, 52, and 54.

In the case where the inner layer of the release sheet 16 is composed of a thermoplastic material that melts at a predetermined temperature, and the support 18 of the adhesive tape 14 is formed of a woven fabric, thermal bonding is effective as the temporary attach means. Namely, when heat is applied from the outer surface side of the release sheet 16, the thermoplastic material in the release sheet 16 is molten, permeates into the woven fabric of the support 18 in the adhesive tape 14, and then solidified there. For this reason, the extending portion 30 of the adhesive tape 14 is temporarily attached to the second portion 24 of the release sheet 16. Moreover, even in the case where the release sheet 16 is not thermoplastic, it can be considered that the thermoplastic material is contained in the material of the support 18 thereby to perform thermal bonding.

In the case where the temporary attach portions 50, 52, and 54 are formed by thermal bonding, the release sheet 16 is folded into the state shown in FIG. 2(*c*), the layered portions 38, 40, and 42 of the first portion 22 and the second portion 24 can be heat sealed and simultaneously or continuously thermal bonding can be performed. Accordingly, the effect of improving production efficiency is attained.

Moreover, for the position in which the temporary attach portion is disposed, as shown in FIG. 1, it is suitable that the temporary attach portion is formed on not only the line along the first sealed portion 38 but also the line along the second sealed portion 40 and the line along the third sealed portion 42. Thereby, even if the first portion 22 of the release sheet 16 is pulled off from the second portion 24 thereof in the traverse direction, the temporary attaching effect can be guaranteed. The lines on which the temporary attach portions 50, 52, and 54 are disposed are not limited to straight lines. The lines may be curves, or may be disposed on multiplets. Furthermore, it can be thought that the lines are disposed in a staggered pattern, a zigzag pattern, or a random patter as long as the lines are aligned with the first sealed portion 38, the second sealed portion 40, and the third sealed portion 42, respectively.

If the adhesive force is excessively increased by the temporary attach portion, a problem that the adhesive tape 14 is difficult to release from the release sheet 16 in application to the portion for application may arise. Then, the adhesive force of the extending portion 30 of the adhesive tape 14 to the release sheet 16 is preferably larger than the adhesive force (tackiness) of the adhesive agent layer 12 to the release sheet 16. Namely, the adhesive force of the support 18 to the release sheet 16 through the temporary attach portions 50, 52, and 54, the adhesive force (tackiness) of the adhesive agent layer 12 of the adhesive tape 14 to the portion for application, and the adhesive force of the adhesive agent layer 12 of the adhesive tape 14 to the release sheet 16 are in a relation as follows.

the adhesive force of the adhesive agent layer 12 to the portion for application
>the adhesive force of the support 18 to the release sheet 16 through the temporary attach portions 50, 52, and 54
>the adhesive force of the adhesive agent layer 12 to the release sheet 16

In the case where the temporary attach portion is in a continuous band-like shape, it can be thought that the amount of the thermoplastic material in the release sheet 16 to be impregnated into the woven fabric of the support 18 in the adhesive tape 14 is excessively large, and it is difficult to obtain the relationship above. Then, in the present invention, as shown in FIGS. 1 to 3 by symbols 50, 52, and 54, the temporary attach portion is discontinuously formed to adjust the number and size of temporary attach portions. Thereby, the adhesive force of the temporary attach portion can be easily adjusted. Thereby, the production efficiency of the pressure-sensitive adhesive tape package 10 is further improved, and constant quality can be ensured in the action effect.

The temporary attaching portions 50, 50, and 54 are preferably formed by thermal bonding. However, a double-sided adhesive tape, an adhesive agent, an adhesive, or pseudoadhesion can be used as the temporary attaching portions. Also, welding, hard pressing, pressing, or a hot-melt adhesive can be used according to the material, shape or the like of the release sheet 16 or the support 18. Here, the pseudoadhesion refers to those that usually have no adhesiveness or tackiness, but bond objects on a special process condition or the like as described in the Patent Map for Technical Fields, General 21 "Adhesion," p. 336, available from the Japan Patent Office website mentioned below, and a pseudoadhesive prepared by adding an additive to an adhesive agent is used.

Further, it is preferable that the release sheet 16 has means for reducing an adhesive force that reduces an adhesive force between the adhesive agent layer 12 of the first portion 26 of the adhesive tape 14 and the release sheet 16. This means for reducing an adhesive force aims at making a first portion 26 of the adhesive tape 14 be easily released off from the release sheet 16 at the time of opening the pressure-sensitive adhesive tape package 10; for this reason, only a portion of the release sheet 16 that the first portion 26 of the adhesive tape 14 contacts may be subjected to the releasing treatment, or only a part of the portion may be subjected to the releasing treatment as long as the purpose can be attained.

Examples of the releasing treatment include, other than a method using a release agent, a method such as embossing and sanding that physically makes releasing easy. As the release agent, any of silicone release agents, alkyl pendant release agents, condensed wax release agents, and the like can be used; among these, the silicone treatment using the silicone release agent is preferable. The silicone treatment is advantageous in that it is performed relatively easily and at low cost. By performing the silicone treatment, in corporation with said the temporary attach portions 50, 52, and 54, upon use of the pressure-sensitive adhesive tape package 10, when the release sheet 16 is opened, the adhesive agent layer 12 is easily removed from the release sheet 16 to expose the adhesive agent layer 12; for this reason, application to the portion for application is easy.

Next, with reference to FIGS. 4 and 5, the action of the pressure-sensitive adhesive tape package 10 according to the present embodiment will be described.

Figure 4:
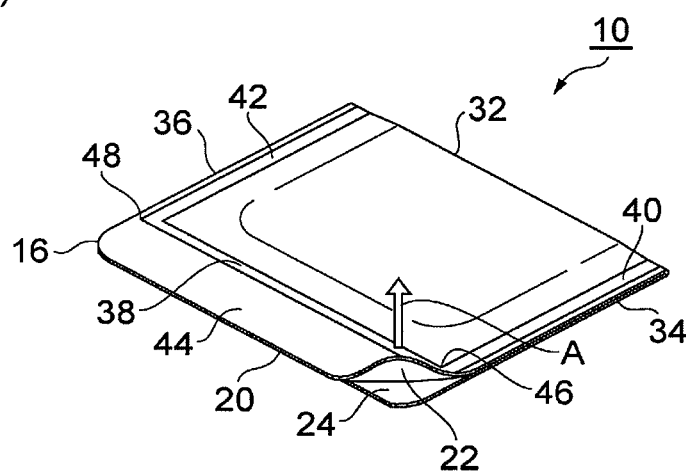
FIGS. 4(a) and 4(b) are perspective views showing a method for using the pressure-sensitive adhesive tape package in FIG. 1.
Figure 4:
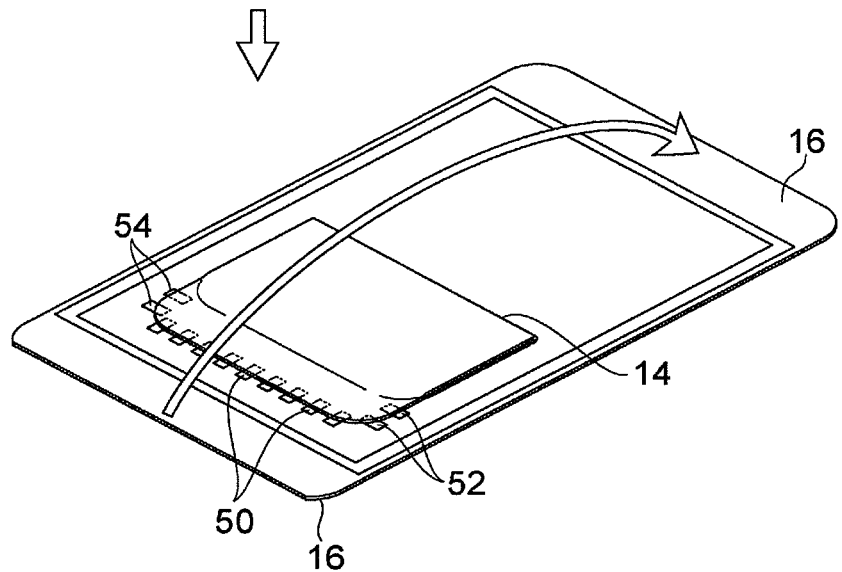
Figure 5:
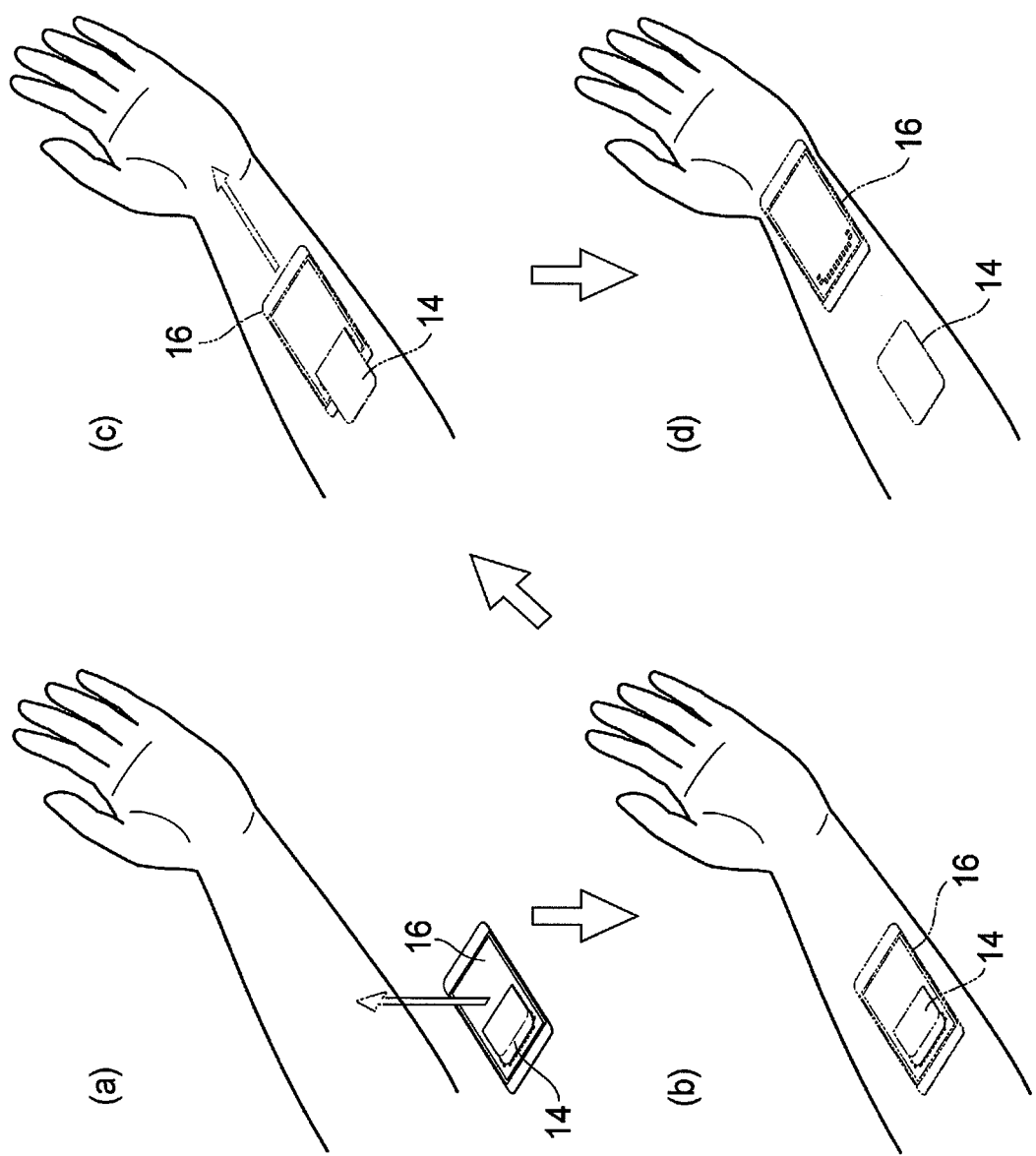
FIGS. 5(a) to 5(d) are drawings illustrating scenes in which an adhesive tape is applied to a portion for application using the pressure-sensitive adhesive tape package in FIG. 1.

FIG. 4(*a*) shows a perspective view of the pressure-sensitive adhesive tape package 10 according to the present embodiment. From this state, a user holds the holding portion 44 of the release sheet 16 (fingers are not shown), and starts to pull off the first portion 22 of the release sheet 16 from the second portion 24 in the direction of an arrow A. At this time, the edge 20 of the first portion 22 of the release sheet 16 is slightly displaced from the edge 20 of the second portion 24 thereof. For this reason, it is easy to hold these portions with fingers, and the first portion 22 can be easily separated from the second portion 24.

Generally, such a pressure-sensitive adhesive tape package 10 is mostly opened from the edge. Accordingly, if the package 10 is started to open from the corner as shown in FIG. 4(*a*), the force concentrates on the corner 46 of the traverse sealed portion 40 and the longitudinal sealed portion 38, and breakage of the sealed portions 38 and 40 is easily started. Once the breakage in the sealed portions 38 and 40 is started, breakage propagates to other portions from the breakage start point as a starting point without additionally applying a large force to break the entire sealed portions 38, 40, and 42. Finally, the pressure-sensitive adhesive tape package 10 reaches the state in FIG. 4(*b*). As described above, the first portion 26 of the adhesive tape 14 is primarily held on the side of the second portion 24 of the release sheet 16 by existence of the temporary attach portions 50, 52, and 54. As a result, the adhesive agent layer 12 in the first portion 26 of the adhesive tape 14 is exposed.

Here, in the case where no space is provided between the longitudinal sealed portion 40 and the edge 34, it is also thought that the force applied to the holding portion 44 acts to the linear portion of the traverse sealed portion 38 to be dispersed, and it is difficult to open the package. With the configuration according to the present embodiment, this point is improved.

Moreover, in the case where breakage starts from the corner 46 of the traverse sealed portion 40 and the longitudinal sealed portion 38, the force acts to the places subjected to temporary attachment in the traverse direction (direction parallel to the edge 20). At this time, if only the temporary attach portion 50 is provided in the traverse direction, the temporary attach portion 50 may not resist the force in the traverse direction. In the present embodiment, the temporary attach portion 52 in the longitudinal length is provided, and the first portion 26 of the adhesive tape 14 can be held if the force in the traverse direction acts.

Unlike FIG. 4, the package may be opened from the corner on the opposite side, the pressure-sensitive adhesive tape package 10 according to the present embodiment is laterally symmetric, and can be opened with a small force in the same manner as above to expose the adhesive agent layer 12 in the first portion 26 of the adhesive tape 14. Moreover, in the case where the center of the holding portion 44 is held and the package is opened, the portion held with fingers is wide, and a large force can act to the traverse sealed portion 28 because of the size of the portion. The package can also be opened without difficulties in this case, although inferior to the opening from the corner.

FIGS. 5(a) to 5(d) show aspects in the case where the adhesive tape of the present invention is used particularly as the patch preparation for medical care or cosmetics, while the adhesive tape of the present invention can also be applied by the same method in the case of use in other application. Namely, FIGS. 5(a) to 5(d) show a method for applying to the portion for application a pressure-sensitive adhesive tape package in which the adhesive agent layer 12 of the first portion 26 of the adhesive tape 14 is exposed. First, the pressure-sensitive adhesive tape package is held by one hand, and placed in the portion for application or in the vicinity of the portion for application as shown in FIGS. 5(a) and 5(b). Next, as shown in FIG. 5(c), while the first portion 22 of the release sheet 16 is held, the release sheet 16 is pulled along the skin in the longitudinal direction thereof and a direction away from the adhesive tape 14. As the release sheet 16 is pulled away, the second portion 28 of the adhesive tape 14 is released from the release sheet 16 and simultaneously applied to the portion for application. Particularly, because the adhesive tape 14 is applied while the release sheet 16 is pulled, the adhesive tape 14 can be applied without a wrinkle. FIG. 5(d) shows the state where the whole adhesive tape 14 is applied to the portion for application to finish application.

The adhesive tape of the present invention can be held by hand because the first portion 22 of the release sheet 16 released off from the adhesive agent layer 12 can be supported by the thumb of the hand on which the adhesive tape is placed. Accordingly, a risk of dropping the adhesive tape when the adhesive tape is applied to the portion for application is small, and worries about shifting of the adhesive tape or hanging of the adhesive tape by gravity in an unintended direction during application are small; for this reason, the adhesive tape can be applied to the portion for application to be targeted for in a carefree manner. The adhesive tape can be easily applied by a single hand even if the portion for application is a back or the like in which application is difficult by oneself.

In the use operation above, a risk of contact of the adhesive agent layer with a skin other than the portion for application is small. Without sticking the adhesive agent layer to the fingers and hands that is often experienced in use of the conventional adhesive tape, it is hygienical; after the first portion 22 of the release sheet 16 is released off, the adhesive tape 14 is supported or reinforced on the second portion 24 of the release sheet 16, therefore preventing the state where the patch preparation cannot be used by adhesion of the adhesive agents to each other.

As above, the suitable embodiment according to the present invention has been described in detail, but the present invention will not be limited to the embodiment above.

Figure 6:
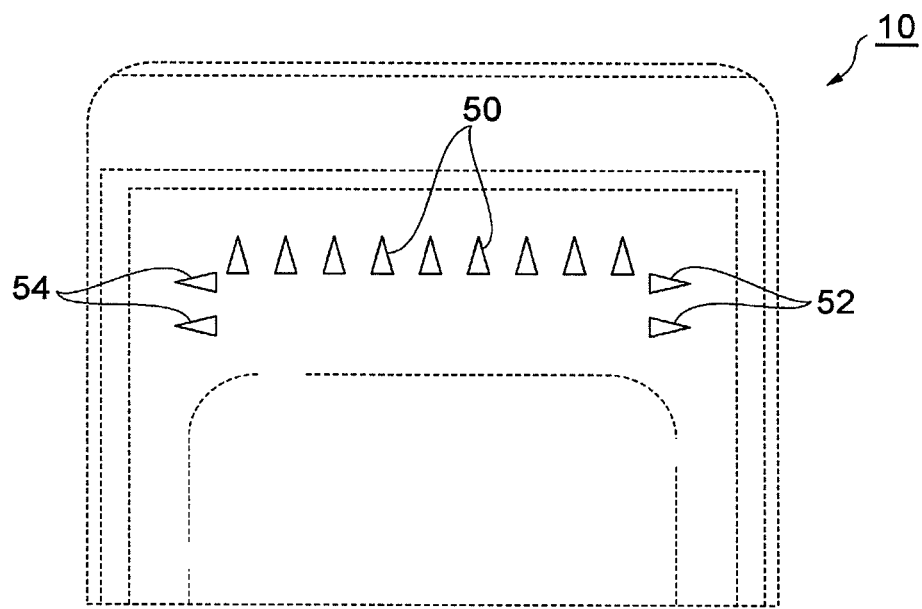
FIGS. 6(a) and 6(b) are drawings showing other shapes of the temporary attach portion, respectively.
Figure 6:
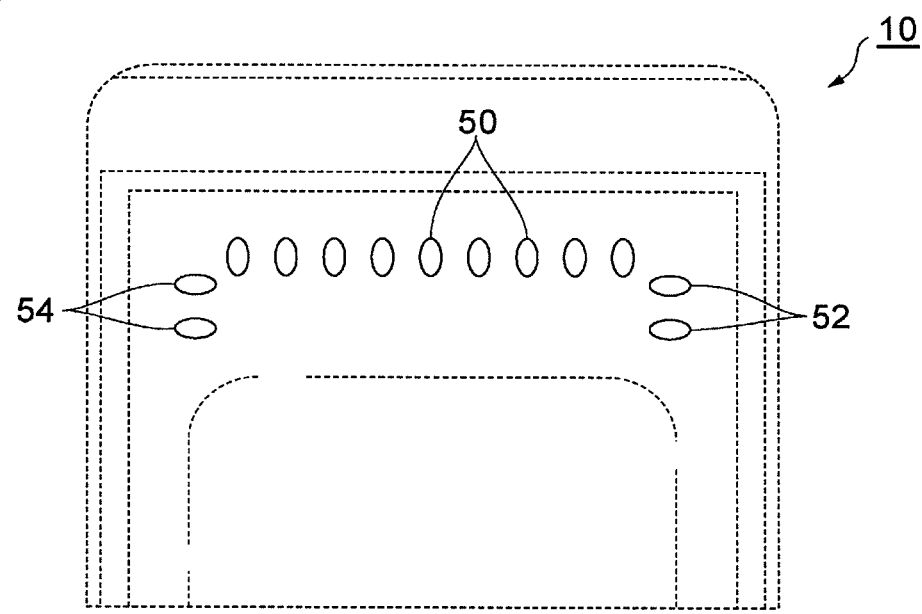

For example, the shapes of the temporary attach portions 50, 52, and 54 are not limited to the rectangular shape shown in FIG. 1, and various shapes such as a triangular shape shown in FIG. 6(a) and an oval shape shown in FIG. 6(b) can be thought.

Moreover, the pressure-sensitive adhesive tape package according to the embodiment above is the three-sealed package type, but a four-sealed package type in which sealing is performed along the bending edge can be produced.

Figure 7:
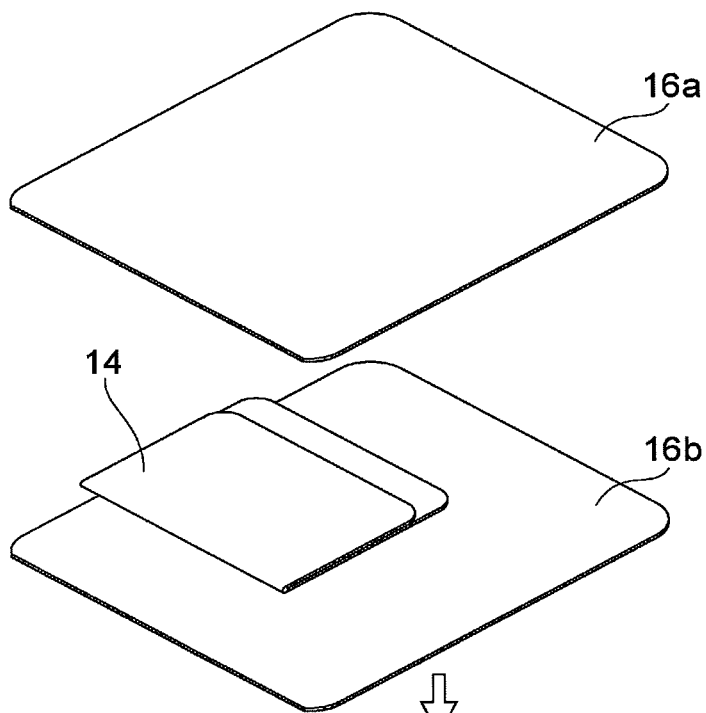
FIGS. 7(a) to 7(c) are perspective views showing production steps of a four-sealed package type pressure-sensitive adhesive tape package.
Figure 7:
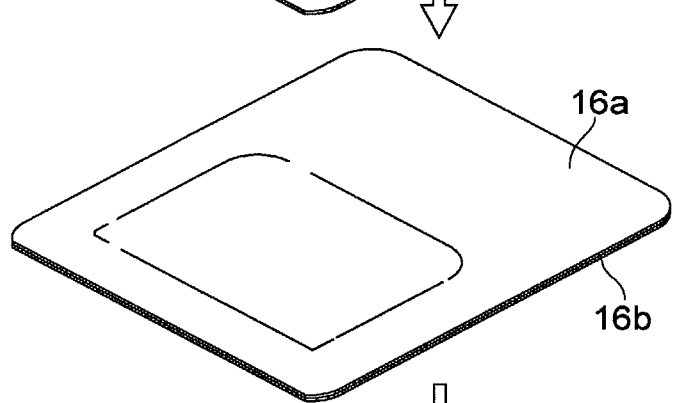
Figure 7:
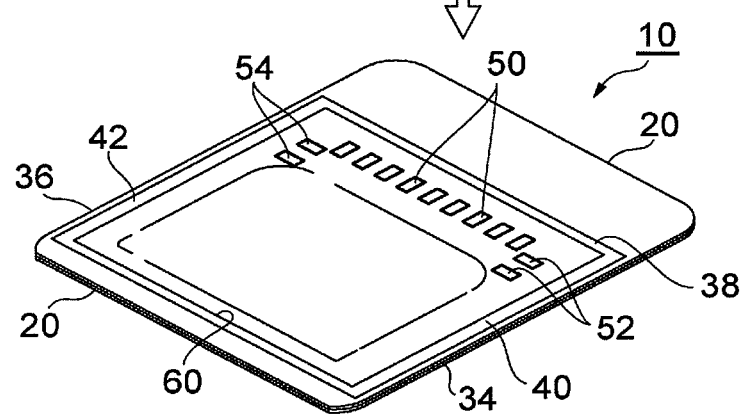

Furthermore, as shown in FIG. 7, a pressure-sensitive adhesive tape package 10 in which two substantially identical release sheets 16a and 16b are prepared, and layered, and the sealed portions 38, 40, 42, and 60 are provided in the four sides may be produced. For the four-sealed package type, the adhesive tape 14 needs to be folded in advance and placed on the release sheet 16b. Moreover, when application is performed, the release sheet 16a needs to be removed from the release sheet 16b. Other functions and the usage method are not different from those in the embodiment above.

REFERENCE SIGNS LIST

10 . . . pressure-sensitive adhesive tape package, 12 . . . adhesive agent layer, 14 . . . adhesive tape, 16, 16a, 16b . . . release sheet, 18 . . . support, 20 . . . first edge, 22 . . . first portion of release sheet, 24 . . . second portion of release sheet, 26 . . . first portion of adhesive tape, 28 . . . second portion of adhesive tape, 30 . . . extending portion, 32 . . . fourth edge, 34 . . . second edge, 36 . . . third edge, 38 . . . first sealed portion, 40 . . . second sealed portion, 42 . . . third sealed portion, 44 . . . holding portion, 46, 48 . . . corner, 50, 52, 54 . . . temporary attach portion, 60 . . . fourth sealed portion.

The invention claimed is:

1. A rectangular pressure-sensitive adhesive tape package accommodating an adhesive tape having a support, and an adhesive agent layer provided on one surface of the support, the pressure-sensitive adhesive tape package comprising a first portion and second portion formed of a release sheet releasably attached to the adhesive agent layer, the first portion and the second portion being layered, a periphery of the layered first portion and second portion being sealed, wherein
 an entire first sealed portion along a first corresponding edge in the pressure-sensitive adhesive tape package, an entire second sealed portion extending along a second corresponding edge adjacent to the first edge and crossing the first sealed portion, and an entire third sealed portion extending along a third corresponding edge adjacent to the first edge and crossing the first sealed portion, are completely spaced from their corresponding edge;
 the adhesive tape is accommodated in the pressure-sensitive adhesive tape package such that the adhesive agent layer faces outwardly in a state where the adhesive tape is folded into a first portion and a second portion;
 the first portion of the adhesive tape is larger than the second portion of the adhesive tape, and has an extending portion extending from the second portion;
 the extending portion is disposed adjacent to the first sealed portion, and temporarily attached with a plurality of temporary attach portions to a portion of the release sheet that is to be the second portion side of the adhesive tape; and
 the plurality of the temporary attach portions is disposed along the first sealed portion, the second sealed portion, and the third sealed portion, and spaced from adjacent temporary attach portions.

2. The pressure-sensitive adhesive tape package according to claim 1, wherein the first sealed portion, the second sealed portion, and the third sealed portion are heat-sealed portions.

3. The pressure-sensitive adhesive tape package according to claim 1, wherein an interval between the first edge and the first sealed portion functions as a holding portion.

4. The pressure-sensitive adhesive tape package according to claim 1, wherein a layer of the release sheet to be located inside of the pressure-sensitive adhesive tape package is formed of a thermoplastic material, and the temporary attach portions are provided by thermal bonding the layer formed of the thermoplastic material to the support of the adhesive tape.

5. The pressure-sensitive adhesive tape package according to claim 1, wherein an adhesive force of the support of the adhesive tape to the release sheet through the temporary attach portions is larger than an adhesive force of the adhesive agent layer to the release sheet.

6. The pressure-sensitive adhesive tape package according to claim 1, wherein means for suppressing an adhesive force that suppresses an adhesive force between the adhesive agent layer of the first portion of the adhesive tape and the release sheet is provided on at least a part of the release sheet.

7. The pressure-sensitive adhesive tape package according to claim 6, wherein the means for suppressing an adhesive force is a silicone-treated surface provided on at least a part of a portion of the release sheet that is attached to the adhesive agent layer of the first portion of the adhesive tape.

8. The pressure-sensitive adhesive tape package according to claim 6, wherein the means for suppressing an adhesive force is an embossed surface and/or sanded surface provided on at least a part of the portion of the release sheet that is attached to the adhesive agent layer of the first portion of the adhesive tape.

9. The pressure-sensitive adhesive tape package according to claim 1, wherein the adhesive tape is used for a skin or a mucous membrane.

10. The pressure-sensitive adhesive tape package according to claim 1, wherein the first portion and the second portion of the release sheet are formed by folding one release sheet.

11. The pressure-sensitive adhesive tape package according to claim 1, wherein the first portion and the second portion of the release sheet are each formed of individual release sheets, and sealed along a fourth edge facing the first edge of the pressure-sensitive adhesive tape package.

* * * * *